United States Patent [19]

Sartori et al.

[11] Patent Number: 4,976,868

[45] Date of Patent: Dec. 11, 1990

[54] POLYESTER MEMBRANES FOR AROMATICS/SATURATES SEPARATION

[75] Inventors: Guido Sartori; W. S. Winston Ho, both of Annandale, N.J.

[73] Assignee: Exxon Research and Engineering Company, Florham Park, N.J.

[21] Appl. No.: 422,216

[22] Filed: Oct. 16, 1989

[51] Int. Cl.$^5$ ............................................. B01D 61/36
[52] U.S. Cl. .................................... 210/640; 210/654
[58] Field of Search ................. 210/634, 649–651, 210/652–654, 500.27, 640; 55/16, 158

[56] References Cited

U.S. PATENT DOCUMENTS 4,861,628  8/1989  Schucker ............................ 210/490

Primary Examiner—Frank Sever
Attorney, Agent, or Firm—Ronald D. Hantman

[57] ABSTRACT

Polyester membranes show good selectivity for aromatics vs. saturates. Modified, e.g., crosslinked, polyesters and their blends can also be used.

3 Claims, One Drawing Sheet

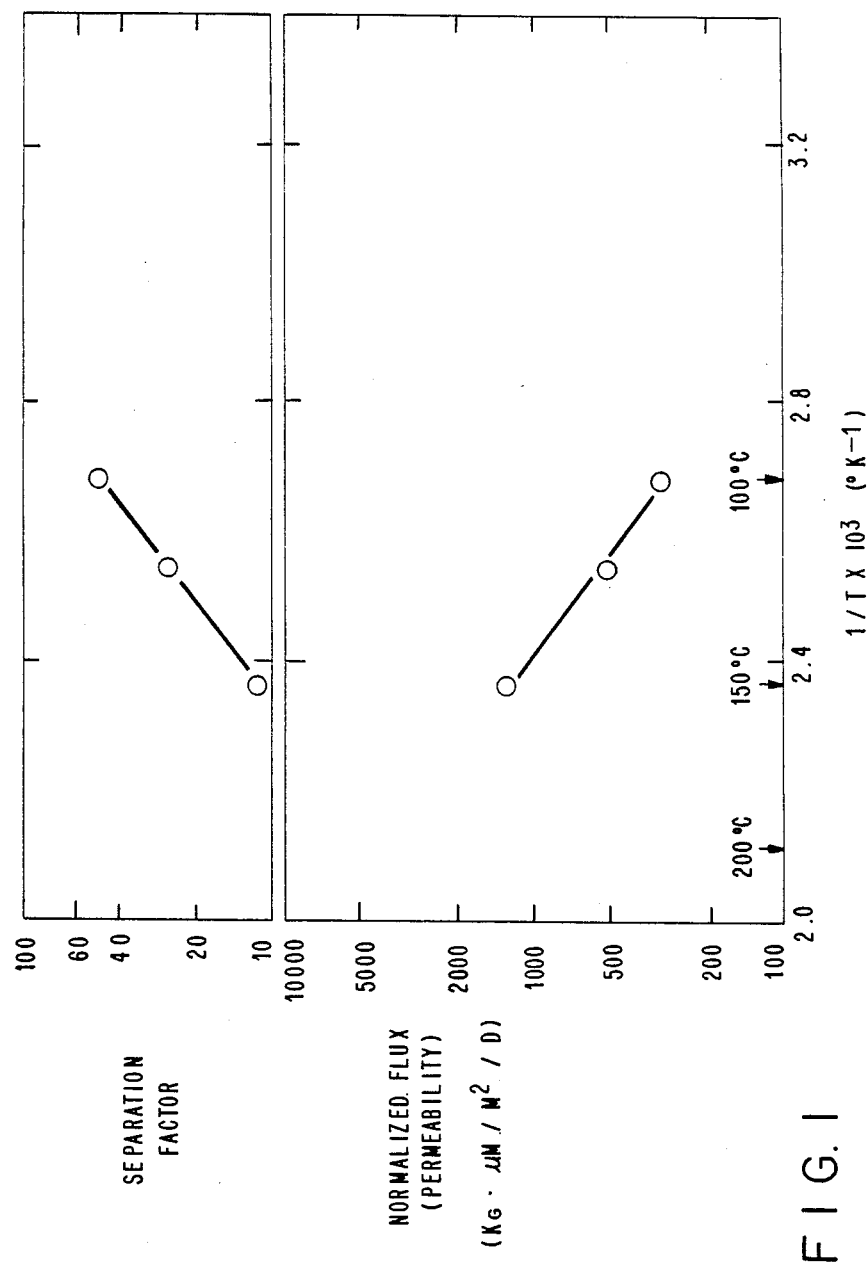
F I G. I

Н4,976,868

POLYESTER MEMBRANES FOR AROMATICS/SATURATES SEPARATION

BACKGROUND

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e., aromatic, unsaturated, saturated, by permeating a portion of the mixture through a non-porous cellulose ether membrane and removing permeate from the permeate side of the membrane using a sweep gas or liquid. Feeds include hydrocarbon mixtures, e.g., naphtha (including virgin naphtha, naphtha from thermal or catalytic cracking, etc.).

U.S. Pat. No. 2,930,754 teaches a method for separating hydrocarbons, e.g., aromatic and/or olefins from gasoline boiling range mixtures, by the selective permeation of the aromatic through certain non-porous cellulose ester membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

The present invention relates to a process for the separation of aromatics from saturates.

Compared to distillation, membrane permeation can lead to considerable energy savings. A membrane can separate a mixture of aromatics and saturates, e.g., a heavy cat naphtha, into a high-octane, mainly aromatic permeate and a high-cetane, mainly saturated retentate. Both permeate and retentate are more valuable than the starting heavy cat naphtha.

SUMMARY OF THE INVENTION

The present invention is a method for separating mixtures of aromatics and non-aromatics into aromatic-enriched and non-aromatic-enriched streams by contacting the aromatics/non-aromatics mixture with one side of a polyester membrane, and selectively permeating the aromatic components of the mixture through the membrane.

BRIEF DESCRIPTION OF THE DRAWINGS

The sole FIGURE shows the toluene/isooctane selectivity and permeability for a membrane according to the present invention.

DESCRIPTION OF THE PREFERRED EMBODIMENT

The present invention is a method for the separation of aromatics from saturates using polyester membranes. Several polyesters are commercially available, e.g., polyethylene terephthalate, polybutylene terephthalate, and polyethylene terephthalate/cyclohexane-dimethanol terephthalate (PETG). That is, PETG is a polyethylene terephthalate in which enough ethylene glycol units have been replaced with 1,2-cyclohexanedimethanol units to make it amorphous.

In the present invention, membranes are used to separate a mixture of aromatics and non-aromatics into an aromatic-enriched fraction and a non-aromatic-enriched fraction.

The membranes are useful for the separation of aromatics from saturates in petroleum and chemical streams, and have been found to be particularly useful for the separation of large substituted aromatics from saturates as are encountered in heavy cat naphtha streams. Other streams which are also suitable feed streams for aromatics from saturates separation are intermediate cat naphtha streams boiling at 93°–160° C., light aromatics content streams boiling in the $C_5$–150° C. range, light catalytic cycle oil boiling in the 200°–345° C. range as well as streams in chemical plants which contain recoverable quantities of benzene, toluene, xylenes (BTX) or other aromatics in combination with saturates. The separation techniques which may successfully employ the membranes of the present invention include perstraction and pervaporation.

Perstraction involves the selective dissolution of particular components contained in a mixture into the membrane, the diffusion of those components through the membrane and the removal of the diffused components from the downstream side of the membrane by the use of a liquid sweep stream. In the perstractive separation of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefore, would include, for example, $C_3$ to $C_6$ saturated hydrocarbons and lube basestocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction and relies on vacuum on the permeate side to evaporate the permeate from the surface of the membrane and maintain the concentration gradient driving force which drives the separation process. As in perstraction, the aromatic molecules present in the feed dissolve into the membrane film, migrate through said film and emerge on the permeate side under the influence of a concentration gradient. Pervaporative separation of aromatics from saturates can be performed at a temperature of about 25° C. for the separation of benzene from hexane but for separation of heavier aromatic/saturate mixtures, such as heavy cat naphtha, higher temperatures of at least 80° C. and higher, preferably at least 100° C. and higher, more preferably 120° C. and higher should be used. Temperatures of about 150° C. have been successfully used with polyester membranes of the present invention, the maximum upper limit being that temperature at which the membrane is physically damaged. Vacuum on the order of 1–50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

When the membrane is used in a hollow fiber configuration with the feed introduced on the exterior side of the fiber, the sweep liquid flows on the inside of the hollow fiber to sweep away the permeated highly aromatic species, thereby maintaining the desired concentration gradient. The sweep liquid, along with the aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering of temperature.

Polyester films are commercially available or can be obtained by preparing a solution in a suitable solvent, e.g., hexafluoroacetone, hexafluoroisopropanol or trifluoroacetic acid, casting on a glass plate or a porous support, adjusting the thickness with a casting knife and drying the membrane first at room temperature, then at high temperature, e.g., 120° C.

The present invention will be better understood by reference to the following examples which are offered by way of illustration and not limitation.

In the following examples, membranes are used to separate toluene from isooctane in a pervaporation apparatus. The initial mixture contains approximately equal weights of the two hydrocarbons.

The pervaporation apparatus is a cell, separated into two compartments by a porous metal plate, on which the membrane is supported. During a pervaporation experiment the aromatics/saturates mixture is circulated through the upper compartment at the desired temperature. The lower compartment is kept at reduced pressure. The permeate is collected in a trap cooled with dry ice-acetone or dry ice-isopropanol and periodically analyzed by gas chromatography.

The following examples illustrate the invention.

EXAMPLE 1

A film of polyethylene terephthalate produced by DuPont under the name of Mylar was used in the pervaporation apparatus described above for the separation of the mixture containing 50 wt% toluene and 50 wt% isooctane. At 170° C. the toluene/isooctane separation factor was about 23, and the normalized flux was 108 Kg.$\mu$M/M$^2$/day. At 200° C. the separation factor was about 18 and the normalized flux was 190 Kg.$\mu$M/M$^2$/day.

EXAMPLE 2

A film of PETG, polyethylene terephthalate/cyclohexane-dimethanol terephthalate, supplied by Acrilex using PETG copolyester 6763 manufactured by Eastman Chemical was used in the pervaporation apparatus described above for the separation of the mixture containing 50 wt% toluene and 50 wt% isooctane. The FIGURE shows the toluene/isooctane selectivity along with the permeability for the PETG membrane as a function of temperature. As shown in this FIGURE, this membrane had a high selectivity of about 50 and a permeability of about 300 Kg.$\mu$M/M$^2$/day at 100° C. The selectivity decreased whereas the permeability increased with increasing temperature. At 150° C., this membrane still had a good selectivity of about 12 and a permeability of about 1300 Kg.$\mu$M/M$^2$/day.

What is claimed is:

1. A method for separating mixtures of aromatics and non-aromatics into aromatic-enriched and non-aromatic-enriched streams comprising:
    (a) contacting said aromatics/non-aromatics mixture with one side of a membrane consisting essentially of a polyester, and
    (b) selectively permeating the aromatic components of the mixture through the membrane.

2. The method of claim 1 wherein said membrane is polyethylene terephthalate.

3. The method of claim 1 wherein said membrane is polyethylene terephthalate/cyclohexane-dimethanol terephthalate.

* * * * *